United States Patent

Mahieu et al.

[11] Patent Number: 6,001,376
[45] Date of Patent: *Dec. 14, 1999

[54] LIPOPHILIC DERIVATIVES OF AMINO DEOXYALDITOLS, COSMETIC COMPOSITIONS CONTAINING THEM, AND NOVEL ALKYL CARBAMATES

[75] Inventors: Claude Mahieu, Paris; Didier Semeria, Courtry; Danièle Cauwet, Paris; Guy Vanlebberghe, Villevaudé, all of France

[73] Assignee: L'Oreal, France

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/807,918

[22] Filed: Feb. 28, 1997

Related U.S. Application Data

[63] Continuation of application No. 08/356,269, Feb. 15, 1995, abandoned.

[30] Foreign Application Priority Data

Apr. 15, 1993 [FR] France ................... 93 04444

[51] Int. Cl.$^6$ ........................ A61K 7/48
[52] U.S. Cl. .............. 424/401; 424/43; 424/45; 424/59; 424/64; 424/73; 424/70.1; 424/70.2; 424/70.7; 514/844; 514/846; 514/937
[58] Field of Search .................. 424/401, 450, 424/43, 45, 64, 59, 73, 70.1, 70.2, 70.7; 514/844, 846, 937

[56] References Cited

U.S. PATENT DOCUMENTS

| | | |
|---|---|---|
| 2,808,402 | 10/1957 | Boettner . |
| 5,009,814 | 4/1991 | Kelkenberg et al. ............ 252/548 |
| 5,254,281 | 10/1993 | Pichardo et al. ............ 252/108 |
| 5,354,510 | 10/1994 | Vanlerberghe et al. ............ 252/548 |
| 5,788,992 | 8/1998 | Mahieu et al. ............ 424/70.1 |

FOREIGN PATENT DOCUMENTS

| | | |
|---|---|---|
| 0220676 | 5/1987 | European Pat. Off. . |
| 0285768 | 10/1988 | European Pat. Off. . |
| 0577506 | 1/1994 | European Pat. Off. . |
| 9205764 | 4/1992 | WIPO . |
| 9213059 | 8/1992 | WIPO . |

Primary Examiner—Jyothsna Venkat
Attorney, Agent, or Firm—Cushman Darby & Cushman IP Group of Pillsbury Madison & Sutro

[57] ABSTRACT

Use in cosmetics of lipophilic derivatives of amino deoxyalditols, cosmetic compositions containing them, and novel alkyl carbamates.

The invention is characterized by the use in cosmetic compositions of one or more lipophilic derivatives of amino deoxyalditols corresponding to the general formula:

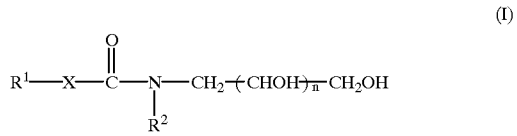

(I)

in which:
 $R^1$ is a saturated linear $C_{14}$–$C_{40}$ aliphatic radical;
 $R^2$ is a hydrogen atom or a linear $C_1$–$C_6$ alkyl radical;
 X is an oxygen atom or a methylene radical; and
 n is an integer from 1 to 5;
with the proviso that when X is a methylene radical $R^1$ contains from 19 to 39 carbon atoms.

Application to the preparation of cosmetic compositions for the treatment of keratinous substances and for buccodental hygiene.

24 Claims, No Drawings

LIPOPHILIC DERIVATIVES OF AMINO DEOXYALDITOLS, COSMETIC COMPOSITIONS CONTAINING THEM, AND NOVEL ALKYL CARBAMATES

This is a continuation of application Ser. No. 08/356,269, filed Feb. 15, 1995 now abandoned.

The subject of the present invention is the use in cosmetics of lipophilic derivatives of amino deoxyalditols, and cosmetic compositions containing one or more of these derivatives.

It is known that mammalian hairs contain a certain number of lipid compounds the structure and distribution of which are not yet fully defined. Along with apolar lipids secreted by the sebaceous glands and for a long time considered to be the only lipids present on the hairs, the presence of other, polar lipids has been demonstrated; among these are cholesterol sulfate, fatty acids and fatty alcohols. These polar compounds have long evaded the investigations of researchers, probably due to their very low solubility in the usual extraction solvents, based on chloroform, methanol and hexane. Their extraction is so difficult that it is even suspected by some that (for some of them) they are covalently bonded to the cell surfaces (P. W. WERTZ. Lipids 23 No. 9 (1988) 878–881).

In man, frequent washing, wear, climatic aggressions and certain cosmetic treatments to which the hair, the eyelashes and the beard are subjected are responsible for the decrease in the esthetic properties of the hairs in general.

It was thus seen to be necessary in the cosmetics field, and in particular for compositions for treating the hair, to repair the damage suffered by the provision of polar lipid products which, on account of their very low solubility in water, will not be removed during washing, even more so since their strong polarity will allow them to become associated with the very structure of the hair, this case not being possible with weakly polar or non-polar compounds of waxy type which are often recommended for improving the condition of the hair.

Certain compounds obtained by extraction from animal or plant tissues have already been recommended for this type of application. In particular, products such as ceramides have been described in the document EP-A-278 505. However, the difficulty in obtaining them in industrial amounts with a sufficient degree of purity makes the use of these compounds unattractive.

Document WO 92/05764 describes shampoo compositions containing at least 1% by weight of a surface-active agent chosen from polyhydroxylated fatty acid amides corresponding to the formula:

in which $R^1$ represents hydrogen, a $C_1$–$C_4$ carbon/hydrogen-based radical, 2-hydroxyethyl, 2-hydroxypropyl or mixtures thereof, and preferably the methyl radical; $R^2$ is a $C_5$–$C_{31}$ carbon/hydrogen-based residue, preferably a $C_7$–$C_{19}$ straight-chain alkyl or alkenyl, even better a $C_9$–$C_{17}$ straight-chain alkyl or alkenyl, and most particularly a $C_{11}$–$C_{15}$ straight-chain alkyl or alkenyl, or mixtures thereof; and Z is a polyhydroxylated carbon-based residue having a linear carbon/hydrogen-based chain with at least 3 hydroxyls attached to the chain, or an alkoxylated derivative (preferably ethoxylated or propoxylated) of the latter. The polyhydroxylated fatty acid amides used as surface-active agents in the shampoo compositions of document WO 92/05764 must, on account of their detergent properties, have an acceptable solubility in water, and it is consequently recommended to use polyhydroxylated fatty acid amides having $C_{12}$–$C_{18}$ $R^2$ substituents, which give materials having the best compromise between the ease of manufacture, the solubility in water and the detergent activity.

It was thus seen to be necessary to search for fully defined synthetic compounds which are solid at the temperatures of use, in order to restructure the hairs without giving them an undesirable oily appearance, and which furthermore are insoluble in water alone but may be placed on the hair using a formula which is essentially aqueous. After being placed on the hair, these compounds will have to provide excellent properties thereto, such as untangling, shine, liveliness and pleasant feel.

The Applicant has found that compounds corresponding particularly well to the above set of criteria were lipophilic derivatives of amino deoxyalditols and more particularly nonionic compounds of linear polyol type combined with a long fatty chain, the two sequences of these amphiphilic compounds being linked by functional groups which are themselves highly polar, of amide or carbamate type.

Furthermore, these compounds proved to be advantageous in the formulation of compositions for buccodental and body hygiene.

Consequently, one subject of the present invention is the use of the above derivatives in cosmetic compositions.

The subject of the invention is also the cosmetic compositions containing such compounds, as well as their application for treating keratinous substances such as the skin or the hair, and for buccodental hygiene.

The subject of the invention is also novel lipophilic derivatives of amino deoxyalditols, of carbamate type, which may be used in the compositions according to the invention.

Other subjects of the invention will become apparent on reading the description and the examples which follow.

The lipophilic Derivatives of amino deoxyalditols used in accordance with the invention in cosmetic compositions, in particular for treating the skin, the hair or for buccodental hygiene, are characterized in that they correspond to the general formula:

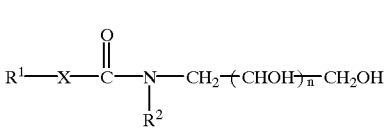

in which
  $R^1$ is a saturated linear $C_{14}$–$C_{40}$ aliphatic radical;
  $R^2$ is a hydrogen atom or a linear $C_1$–$C_6$ alkyl radical;
  X is an oxygen atom or a methylene radical; and
  n is an integer from 1 to 5, with the proviso that when X is a methylene radical $R^1$ is a saturated linear $C_{19}$–$C_{39}$ aliphatic radical.

Some of the compounds corresponding to the general formula (I) above are known. In particular, U.S. Pat. Nos. 1,985,424 and 2,703,798 describe amides corresponding to this general formula. However, the only compounds described correspond to short or medium-length lipophilic chains limited to 18 carbon atoms.

U.S. Pat. No. 2,040,997 describes carbamates corresponding to the formula (I) above. These carbamates correspond to the general formula

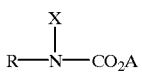

in which R is an aliphatic radical containing polyhydroxy substitutions, X is a hydrogen atom or an alkyl radical and A is an aliphatic hydrocarbon radical having 8 or more carbon atoms. A preferably represents a straight-chain alkyl group having 10 to 20 carbon atoms. The carbamates used as synthetic intermediates are illustrated only by the sole dodecyl compound.

In the formula (I) above, and when X represents an oxygen atom, $R^1$ represents a saturated linear $C_{14}$–$C_{40}$, preferably a $C_{14}$–$C_{32}$ and even better a $C_{16}$–$C_{22}$, aliphatic radical. When X represents a methylene radical, $R^1$ represents a saturated linear $C_{19}$–$C_{39}$, preferably a $C_{21}$–$C_{29}$, aliphatic radical, $R^2$ represents a hydrogen atom or a linear $C_1$ to $C_6$ alkyl radical, preferably methyl; and n is an integer from 1 to 5 and preferably equal to 4.

Among the recommended derivatives of formula (I) there may be mentioned 1-[docosanoyl-methyl-amino]-1-deoxy-D-glucitol, [hexadecyloxycarbonyl-methyl-amino]-1-deoxy-D-glucitol, 1-[octadecyloxycarbonyl-methyl-amino]-1-deoxy-D-glucitol, 1-[docosyloxycarbonyl-methyl-amino]-1-deoxy-D-glucitol, and 1-[tetracosanoyl-methyl-amino]-1-deoxy-D-glucitol.

There may also be mentioned the amides derived from mixtures of fatty acids or the carbamates derived from a mixture of fatty alcohols; fatty alcohols or acids may be obtained by synthesis or by extraction from natural, plant or animal waxes.

As an example, octacosanol extracted from rice seeds or from wheat and sold by the company NIPPON OILS is a mixture of $C_{26}$–$C_{36}$ alcohols. Mixtures of $C_{22}$- and $C_{24}$-rich acids may be obtained, inter alia, from rice wax, carnauba wax or beeswax.

The processes for preparing the derivatives of formula (I) above are well known to those skilled in the art. It is possible, for example, to prepare the amides corresponding to the formula (I) by the method described by E. K. Hildreth, Biochem J. 207 (1982) 363.

According to this method, a mixed anhydride is prepared in a first phase by reacting an acid of formula $R^1COOH$, where $R^1$ is defined as above, with a lower alkyl haloformate, preferably an ethyl haloformate, in a suitable solvent in the presence of a base, for example pyridine, in order to form a mixed anhydride solution.

In a second phase, the mixed anhydride solution obtained is reacted with an N-alkylamine of formula:

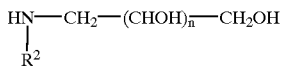

where $R^2$ and n are defined as above, in a suitable solvent, for example alkanols such as methanol or ethanol, or alternatively dimethylformamide.

The carbamates corresponding to the formula (I) may be prepared by reacting an amine of formula

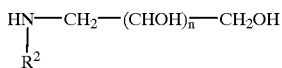

where $R^2$ and n are defined as above, with a suitable $C_{14}$–$C_{40}$ alkyl haloformate, for example a chloroformate, in the presence of sodium hydrogen carbonate, water and a suitable solvent, for example tetrahydrofuran.

The present invention also relates to novel carbamates falling within the scope of the general formula (I) above. More particularly, these novel carbamates correspond to the general formula (II)

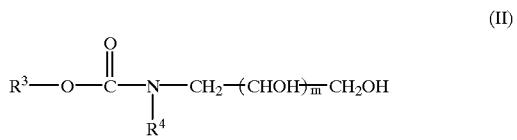

in which $R^3$ is a saturated linear $C_{22}$–$C_{40}$, preferably a $C_{22}$–$C_{26}$, aliphatic radical, $R^4$ is a hydrogen atom or a linear $C_1$–$C_6$ alkyl radical and m is an integer from 1 to 5, preferably equal to 4.

Preferably, $R^3$ is the docosyl radical and $R^4$ is a methyl radical.

Cosmetic compositions, in particular the compositions for treating the hair and the skin and for buccodental hygiene, in accordance with the invention, are characterized in that they contain at least one derivative corresponding to the formula (I) above in a cosmetically acceptable support.

When the compositions according to the invention are used for treating the hair, an improvement in the untangling of wet hair and the provision of softness and smoothness to dried hair are observed.

Generally, the compound or compounds of formula (I) are present in the composition at a concentration between 0.01 and 15% by weight relative to the total weight of the composition, and preferably at a concentration of 0.1 to 10% by weight relative to the total weight of the composition.

The cosmetically acceptable support may consist of a fatty phase or of an aqueous medium which consists solely of water or of a mixture of water and a cosmetically acceptable solvent, such as a $C_1$–$C_4$ lower alkyl, for instance ethanol, isopropanol or n-butanol; alkylene glycols, for instance ethylene glycol; glycol ethers.

The compositions according to the invention may be provided in the form of an emulsion (a milk, cream or an ointment), a vesicle dispersion, a solid stick, an aqueous solution or dispersions which are optionally thickened or gelled, aerosol foams or spray.

The compositions may additionally contain surface-active agents which are well known in the state of the art, such as anionic, nonionic, cationic, amphoteric or zwitterionic surface-active agents or mixtures thereof.

The compositions are, for example, emollient lotions, milks or creams, milks or creams for skin care or for hair care, creams, lotions or milks for removing make-up, foundation bases, antisun lotions, milks or creams, lotions, milks or creams for artificial tanning, shaving creams or foams, after-shave lotions, shampoos, conditioners or mascaras.

These compositions may also be provided in the form of sticks for the lips, intended either to color them or to prevent chapping, or in the form of make-up products for the eyes or powders and foundations for the face.

When the compositions according to the invention are provided in the form of emulsions of the water-in-oil type or oil-in-water type, the fatty phase consists essentially of a mixture of compound of formula (I) with at least one oil, and optionally another fatty substance.

The fatty phase of the emulsions may constitute 5 to 60% of the total weight of the emulsion.

The aqueous phase of the said emulsions preferably constitutes 30 to 85% of the total weight of the emulsion.

The proportion of the emulsifying agent may be between 1 and 20%, and preferably between 2 and 12%, of the total weight of the emulsion.

When the compositions according to the invention are provided in the form of oily, oleo-alcoholic or aqueous-alcoholic lotions, they may consist of, for example, antisun lotions containing a screening agent for absorbing UV rays, or of emollient solutions for the skin; the oily lotions may also consist of foaming oils containing an oleo-soluble surfactant, or of bath oils, etc.

Among the main adjuvants which may be present in the compositions according to the invention, there may be mentioned fatty substances such as mineral, animal or plant oils or waxes, fatty acids, fatty acid esters such as fatty acid triglycerides which have from 6 to 18 carbon atoms, or fatty alcohols; emulsifying agents such as oxyethylenated fatty alcohols or polyglycerol alkyl ethers, solvents such as lower monoalcohols or polyalcohols containing from 1 to 6 carbon atoms, or alternatively water.

The mono- or polyalcohols which are more particularly preferred are chosen from ethanol, isopropanol, propylene glycol, glycerol and sorbitol.

By way of fatty substances, among the mineral oils there may be mentioned liquid paraffin; among the animal oils there may be mentioned whale oil, seal oil, menhaden oil, halibut liver oil, cod oil, tuna oil, tortoise oil, ox foot oil, horse foot oil, sheep foot oil, mink oil, otter oil, marmot oil, etc.; among the plant oils there may be mentioned almond oil, wheatgerm oil, olive oil, corn germ oil, jojoba oil, sesame oil, sunflower oil, palm oil, walnut oil, karite oil, shorea oil, macadamia oil, blackcurrant seed oil and the like.

Among the fatty acid esters, it is possible to use the saturated or unsaturated $C_{12}$ to $C_{22}$ acid esters of lower alcohols such as isopropanol or glycerol or of saturated or unsaturated, linear or branched $C_8$ to $C_{22}$ fatty alcohols or alternatively of $C_{10}$–$C_{22}$ 1,2-alkanediols.

As fatty substances, there may also be mentioned petrolatum, paraffin, lanolin, hydrogenated lanolin, tallow, acetylated lanolin and silicone oils.

Among the waxes, there may be mentioned Sipol wax, lanolin wax, beeswax, candelila [sic] wax, microcrystalline wax, carnauba wax, spermaceti, cocoa butter, karite butter, silicone waxes, hydrogenated oils which are solid at 25° C., sucroglycerides, and the oleates, myristates, linoleates and stearates of Ca, Mg and Al.

Among the fatty alcohols, there may be mentioned lauryl alcohol, cetyl alcohol, myristyl alcohol, stearyl alcohol, palmityl alcohol and oleyl alcohol and GUERBET alcohols such as 2-octyldodecanol, 2-decyltetradecanol or 2-hexyldecanol.

By way of emulsifying agents, among the polyoxyethylenated fatty alcohols there may be mentioned lauryl alcohol, cetyl alcohol, stearyl alcohol and oleyl alcohol containing from 2 to 20 moles of ethylene oxide, and among the polyglycerol alkyl ethers there may be mentioned the $C_{12}$–$C_{18}$ alcohols containing from 2 to 10 moles of glycerol.

It may also be useful to use thickening agents such as cellulose derivatives, polyacrylic acid derivatives, guar gum, carob gum or xanthan gum.

The compositions in accordance with the invention may be provided in the form of a vesicle dispersion of ionic or nonionic amphiphilic lipids. They are especially prepared by swelling the lipids in an aqueous solution in order to form spherules which are dispersed in the aqueous medium, as described in the article BANGHAM, STANDISH & WATKINS, J. Mol. Biol., 13,238 (1965) or in the patents FR-2,315,991 and 2,416,008 of the Applicant.

The various types of preparation processes are described in "Les liposomes en biologie cellulaire et pharmacologie" [Liposomes in cell biology and pharmacology], Edition INSERM/John Liberry Eurotext, 1987, pages 6 to 18.

The composition according to the invention may also contain adjuvants commonly used in cosmetics and especially moisturizing products, emollients, products for treating skin complaints, sunscreen agents, germicides, dyes, preserving agents, fragrances and propellants, and sequestering agents.

The examples which follow are intended to illustrate the invention, without any limitation being implied thereby.

PREPARATION EXAMPLES

Example 1

Preparation of 1-[docosanoyl-methyl-amino]-1-deoxy-D-glucitol

Phase A: Preparation of the mixed anhydride 140 ml of tetrahydrofuran and 23.4 g of ethyl chloroformate are introduced into a reactor, a solution of 70 g of behenic acid sold under the name "PRIFRAC 2989" by the company UNICHEMA dissolved in 140 ml of tetrahydrofuran is added steadily at 40° C., followed by neutralization with 21.8 g of triethylamine, and the solution is filtered, which solution will be used as it is in phase B.

Phase B:

40.1 g of N-methylglucamine are dissolved, at 60° C., in 400 ml of dimethylformamide in a reactor, followed by slow addition of the mixed anhydride obtained in phase A, and the reaction is continued at 60° C. for 3 hours.

At the end of the reaction, the reaction mixture is diluted with 400 ml of water and is cooled to 40° C. After draining the crystallized product, it is recrystallized from 1 l of 95° ethanol. 94.6 g of a white product are obtained, equivalent to a final yield of 88%.

Analyses

Elemental analysis

|  | % C | % H | % N | % O |
|---|---|---|---|---|
| Theoretical | 67.27 | 11.49 | 2.71 | 18.54 |
| Found | 67.44 | 11.36 | 2.75 | 18.43 |

Melting point: 114° C.

Example 2

Preparation of 1-[hexadecyloxycarbonyl-methyl-amino]-1-deoxy-D-glucitol 11.7 g of N-methylglucamine are dissolved in a mixture of 30 ml of water and 40 ml of tetrahydrofuran in a reactor, followed by addition and dispersion of 20 g of sodium hydrogen carbonate.

While maintaining the temperature of the reaction mixture at 20° C., 18.3 g of hexadecyl chloroformate marketed by S.N.P.E. are added dropwise, and the mixture is then left to react for two hours and is diluted with 100 ml of tetrahydrofuran.

The reaction mixture is filtered; the solid product recovered is dissolved in 500 ml of acetone; the insoluble fraction is removed by hot filtration.

After cooling at 1° C. for 12 hours, the crystallized product is recovered and dried. 15.5 g of a pure white product are obtained, equivalent to a final yield of 56%.

Analyses
Elemental analysis

|  | % C | % H | % N | % O |
|---|---|---|---|---|
| Theoretical | 62.17 | 10.65 | 3.02 | 24.16 |
| Found | 62.13 | 10.67 | 3.13 | 24.16 |

Melting point: 80° C.

Example 3

Preparation of 1-[octadecyloxycarbonyl-methyl-amino]-1-deoxy-glucitol

The experimental procedure of Example 2 is repeated, replacing the hexadecyl chloroformate with octadecyl chloroformate. The expected product obtained is white and the final yield is 66%.

Analyses
Elemental analysis

|  | % C | % H | % N | % O |
|---|---|---|---|---|
| Theoretical | 63.51 | 10.86 | 2.85 | 22.78 |
| Found | 63.57 | 10.94 | 2.94 | 22.88 |

Melting point: 85° C.

Example 4

Preparation of 1-[docosyl-oxycarbonyl-methyl-amino]-1-deoxy-D-glucitol 70.2 g of N-methylglucamine are dissolved in a mixture of 180 ml of water and 240 ml of tetrahydrofuran in a reactor, followed by addition and dispersion of 12 g of sodium hydrogen carbonate.

While maintaining the temperature of the reaction mixture at 5° C., 140.1 g of docosyl chloroformate dissolved in 100 ml of tetrahydrofuran are added dropwise over two hours; the reaction mixture is diluted with a further 1 l of tetrahydrofuran and is left to react for two hours.

The reaction mixture is filtered; after separation of the phases once settling has taken place, the organic phase is collected and concentrated, and the residue is then recrystallized from one liter of a mixture of 8 volumes of acetone and 2 volumes of methanol. 70 g of a pure white product are obtained, equivalent to a final yield of 36%.

Analyses
Elemental analysis

|  | % C | % H | % N |
|---|---|---|---|
| Theoretical | 63.71 | 10.93 | 3.23 |
| Found | 63.83 | 10.91 | 3.22 |

Melting point: 94.6° C.

Example 5

Preparation of 1-[Docosanoylamino]-1-deoxy-D-glucitol

The experimental procedure of Example 1 is repeated, replacing the N-methylglucamine with 37.2 g of glucamine; 59 g of the expected product are obtained (Y=57%), by recrystallization from propanol.

Elemental analysis

|  | % C | % H | % N | % O |
|---|---|---|---|---|
| Theoretical | 66.76 | 11.4 | 2.78 | 19.06 |
| Found | 66.7 | 11.4 | 2.58 | 18.92 |

Melting point: 136° C.

The examples which follow are intended to illustrate the cosmetic formulations according to the present invention.

Example 6

Preparation of 1-[tetracosanoyl-methyl-amino]-1-deoxy-D-glucitol

Phase A: preparation of the mixed anhydride 1.55 g of ethyl chloroformate dissolved in 10 ml of tetrahydrofuran are introduced into a reactor.

At 0° C., a solution of 5 g of tetracosanoic acid sold under the name "NAFOL 24/26 Acid" by the company CONDEA and of composition:

$C_{20}$: 5%,
$C_{22}$: 5%,
$C_{24}$: 60%,
$C_{26}$: 22%,
$C_{28}$: 4%, in 50 ml of tetrahydrofuran which has been salified beforehand with 1.44 g of triethylamine, is introduced slowly. The solution is allowed to react for 2 hours and is then filtered, which solution will be used as it is in phase B.

Phase B:

2.6 g of N-methylglucamine are dissolved, at 80° C., in 50 ml of dimethylformamide in a reactor and the temperature is maintained at 60° C.; the mixed anhydride obtained in phase A is then added slowly and the reaction is continued at 60° C. for 3 hours.

The mixture is cooled to 4° C. and is left to crystallize for 1 hour; after filtration, the solid is recrystallized from methanol.

3.2 g of the expected product are thus obtained (Y=43%)
Elemental analysis

|  | % C | % H | % N | % O |
|---|---|---|---|---|
| Theoretical | 68.21 | 11.63 | 2.57 | 17.59 |
| Found | 68.28 | 11.69 | 2.45 | 17.59 |

Melting point: 102° C.

The mass spectrum is in accordance with the expected structure.

Example A

Shampoo

| Compound of Example 1 | 5 g |
|---|---|
| Alkyl ($C_9/C_{10}/C_{11}$ - 20/40/40) (1,4) polyglucoside sold by the company HENKEL at a concentration of 500 g % [sic] of active substance | 15 g AS |
| Preserving agent | qs |
| Fragrance | qs |
| Dye | qs |
| Water | qs 100 g | pH adjusted to 7 with hydrochloric acid
A thickened milky liquid is obtained.

Example B

Shampoo

| | |
|---|---|
| Compound of Example 1 | 0.1 g |
| Sodium lauryl ether sulfate ($C_{12}/C_{14}$ - 70/30) 2.2 mol EO sold under the name "EMPICOL ESB/3 FL" by the company MARCHON at a concentration of 28% of active substance | 15 g AS |
| Cocoyl betaine in aqueous solution at a concentration of 32% | 2.5 g AS |
| Coconut acid monoisopropanolamide sold under the name "EMPILAN CIS" by the company MARCHON | 1 g |
| Cetyl 2-hydroxycetyl-stearyl ether/cetyl alcohol | 2.5 g |
| Fragrance | qs |
| Preserving agent | qs |
| Dyes | qs |
| Water | qs 100 g | pH adjusted to 6.7 with triethanolamine.

A thickened milky liquid is obtained.

Example C

Shampoo

| | |
|---|---|
| Compound of Example 1 | 1.5 g |
| Polyglycerolated dodecanediol containing 3.5 mol of glycerol | 10 g AS |
| Hexanedecanediol ether (3 mol) and polyethylene glycol ether (60 EO) | 2.5 g |
| Preserving agents | qs |
| Fragrance | qs |
| Dyes | qs |
| Water | qs 100 g | pH adjusted to 7.6 with triethanolamine

A thick clear liquid is obtained

Example D

Shower Gel

| | |
|---|---|
| Compound of Example 1 | 0.5 g |
| Lauric acid ($C_{12}/C_{14}$ - 70/30) carboxyl ether 4.5 EO sold under the name "AKYPO RLM 45" at a concentration of 90 g % of active substance by the company RIOIIN | 10 g AS |
| Sodium cocoamidoethyl (N-hydroxyethyl, N-carboxymethyl)glycinate | 5 g AS |
| Sodium lauroyl sarcosinate sold under the name "ORAMIX L 30" by the company SEPPIC at a concentration of 30 g % AS | 8 g AS |
| Dioleate of polyethylene glycol (55 EO) and of propylene glycol/water (40/40/20) sold under the name "ANTIL 141" liquid by the company GOLDSCHMIDT at a concentration of 40 g % AS | 2 g AS |
| Preserving agent | qs |
| Fragrance | qs |
| Dye | qs |
| Water | qs 100 g | pH adjusted to 7.% with hydrochloric acid.

A clear fluid gel is obtained.

Example E

Conditioner

| | |
|---|---|
| Compound of Example 1 | 2 g |
| Distearyldimethylammonium chloride | 2 g |
| Hydroxyethylcellulose sold under the name "NATROSOL 250 HHR" by the company AQUALON | 1 g |
| Preserving agent | qs |
| Fragrance | qs |
| Dye | qs |
| Water | qs 100 g | pH adjusted to 4.5 with triethanolamine.

A white fluid gel is obtained.

Example F

Conditioner

| | |
|---|---|
| Compound of Example 1 | 10 g |
| Distearyldimethylammonium chloride | 5 g |
| Mixture of cetylstearyl alcohol and oxyethylenated cetylstearyl alcohol containing 33 EO (80/20) | 3 g |
| Cetyl alcohol | 1 g |
| Stearyl alcohol | 1 g |
| Preserving agent | qs |
| Fragrance | qs |
| Dye | qs |
| Water | qs 100 g | pH adjusted to 4 with triethanolamine.

A thick white cream is obtained.

Example G

After-Sun Care—Oil-In-Water Emulsion

| | |
|---|---|
| 1-[Docosanoyl-methyl-amino]-1-deoxy-D-glucitol (compound of Example 1) | 0.5 g |
| Glycerine | 3 g |
| Sodium hydroxide | 0.24 g |
| Cetyl alcohol | 2.5 g |
| Ethylenediaminetetraacetic acid (EDTA) | 0.1 g |
| Stearyl alcohol | 1 g |
| Sorbitol | 3 g |
| Sunflower oil | 6 g |
| Polyoxyethylenated sorbitan monolaurate containing 20 mol of ethylene oxide, sold under the name "TWEEN 20" by the company ICI | 2 g |
| Crosslinked polyacrylic acid sold under the name "CARBOPOL 941" by the company GOODRICH | 0.3 g |
| Oily extract of yolk | 2 g |
| Silicone oil sold under the name "SILBIONE ANTIMOUSSE [ANTI-FOAM] 70 452" by the company RHONE POULENC | 0.15 g |
| Beeswax | 1 g |
| Oat flour | 0.5 g |
| Karite butter | 1.5 g |
| Preserving agents, antioxidant, fragrance | qs |
| Water | qs 100 g |

The emulsion is prepared according to the following experimental procedure:
1) Swell "CARBOPOL 941" with glycerine in some water, neutralize to pH 7 with sodium hydroxide at 60° C. with stirring (Phase 1)
2) Add the emulsifying agents TWEEN 20 and oily extract of yolk, and the oat flour to phase 1 (Phase 2)
3) Dissolve EDTA in some water at 60° C.
Add the sorbitol, the karite butter and the beeswax and the silicone oil, with stirring at 60° C.

Leave to stir for 30 minutes (Phase 3)
4) Add phase 2 to phase 3 at 60° C. with stirring (Phase 4)
5) Melt the sunflower oil, the cetyl alcohol and stearyl alcohol co-emulsifying agents, the preserving agents for the fatty phase and compound of Example 1, at 70° C. (Phase 5).
6) Mix phases 4 and 5 with stirring.
7) Allow to cool to 40° C.

Add the preserving agents for the aqueous phase and the fragrance. Continue to stir until completely cooled.

Example H

Direct Dyeing

| | |
|---|---|
| Compound of Example 2 | 0.1 g |
| Propylene glycol monomethyl ether | 10 g |
| Oxyethylenated nonylphenol (9 EO) marketed under the name "RHODIASURF NP 9 OR" by the company RHONE POULENC | 8 g |
| Coconut diethanolamide was [sic] sold under the name "COMPERLAN KD" by the company HENKEL | 2 g |
| N1,N4,N4-tris($\beta$-hydroxyethyl)-1,4-diamino-2-nitrobenzene | 0.5 g |
| 1-Amino-2-nitro-4-B-hydroxyethylamino-benzene [sic] | 0.05 g |
| pH agent | qs pH 9 |
| Demineralized water | qs 100 g |

Mode of application:

The locks of permanent-waved gray hair containing 90% of white hairs are immersed in the dye composition, in a proportion of 20 g of formula per 3 g of hair. The formula is allowed to act for 30 minutes. The hair is then rinsed and dried. The hair is dyed violet.

Example I

Alkaline Oxidation Dye—Cream Support

| | |
|---|---|
| Compound of Example 1 | 0.3 g |
| Cetylstearyl alcohol ($C_{16}/C_{18}$ 50/50) sold under the name CIRE DE LANETTE O by the company HENKEL | 18 g |
| 2-octyldodecanol | 3 g |
| Oxyethylenated cetylstearyl alcohol ($C_{16}/C_{18}$ 35/65) (15 EO) sold under the name "MERGITAL CS 15" by the company SINNOVA-HENKEL | 3 g |
| Ammonium lauryl sulfate at a concentration of 30% AS | 12 g as such |
| Polymer of formula | |

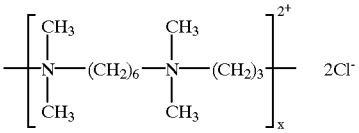

in aqueous solution at a concentration of 60% of active substance, sold under the name

| | |
|---|---|
| "MEXOMER PO" by the company CHIMEX | 3 g as such |
| Ammonium thiolactate (at a concentration of 50% of thiolactic acid equivalent) | 0.8 g |
| Aqueous ammonia at a concentration of 20% of NH3 | 12 g |
| Para-aminophenol | 0.436 g |

| | | |
|---|---|---|
| 1-Methyl-2-hydroxy-4-$\beta$-hydroxyethylamino-benzene | | 0.668 g |
| Demineralized water | qs | 100 g |

Mode of application

The composition obtained is diluted at the time of use with 1.5 times its weight of 20 volume hydrogen peroxide, the pH of which is 3.

The mixture thus prepared is applied to gray hair containing 90% of white hairs, which hair may or may not have been permanent-waved, in a proportion of 28 g per 3 g of hair. The mixture is allowed to act for 30 minutes.

The hair is then rinsed, washed with a shampoo and rinsed. The hair is dyed a coppery color or an intense coppery color depending on whether this is natural or permanent-waved hair respectively.

Example J

Anti-Sun Oil-In-Water Emulsion

| | | |
|---|---|---|
| Compound of Example 2 | | 2 g |
| Stearic acid | | 2 g |
| Stearyl alcohol | | 1 g |
| Liquid paraffin | | 10 g |
| 2-Ethylhexyl para-methoxycinnamate sold under the name "PARSOL MCX" by the company GIVAUDAN | | 5 g |
| Glycerine | | 3 g |
| Sorbitol | | 2 g |
| Acrylic acid/$C_{10}$—$C_{30}$ alkyl acrylate crosslinked copolymer sold under the name "PEMULEN TR-1" by the company GOODRICH | | 0.3 g |
| Triethanolamine | | 0.4 g |
| Preserving agents | qs | |
| Water | qs | 100 g |

Example K

Anti-Sun Oil-In-Water Emulsion

| | | |
|---|---|---|
| Compound of Example 4 | | 2 g |
| Stearic acid | | 2 g |
| Stearyl alcohol | | 1 g |
| Liquid paraffin | | 12.5 g |
| 2-Ethylhexyl para-methoxycinnamate sold under the name "PARSOL MCX" by the company GIVAUDAN | | 2.5 g |
| Glycerine | | 3 g |
| Acrylic acid/$C_{10}$—$C_{30}$ ethyl acrylate crosslinked copolymer sold under the name "PEMULEN TR-1" by the company GOODRICH | | 0.3 g |
| Triethanolamine | | 0.4 g |
| Preserving agents | qs | |
| Water | qs | 100 g |

Example L

Conditioner

| | | |
|---|---|---|
| Compound of Example 6 | | 0.3 g |
| Distearyldimethylammonium chloride | | 2 g |
| Fragrance - dye | qs | |
| Water | qs | 100 g |
| pH adjusted to 5 with sodium hydroxide | | |

Example M

Shampoo

| | | |
|---|---|---|
| Compound of Example 4 | | 3 g |
| Alkyl ($C_9/C_{10}/C_{11}$ - 20/40/40) (1.4) polyglucoside sold at a concentration of 50 g % of active substance by the company HENKEL | | 12 g AS |
| Preserving agent, fragrance, dye | qs | |
| Water | qs | 100 g | pH adjusted to 6 with hydrochloric acid.

A slightly opalescent composition is obtained.

Example N

Deodorant Stick

| | | |
|---|---|---|
| Compound of Example 4 | | 0.2 g |
| Sodium hydroxide | | 1 g |
| Stearic acid | | 5 g |
| Propylene glycol | | 50 g |
| 2,4,4'-Trichloro-2-hydroxydiphenyl ether sold under the name "IRGASAN DP 300" by the company CIBA-GEIGY | | 0.3 g |
| Water | qs | 100 g |

Example O

Styling Lotion

| | | |
|---|---|---|
| Vinylpyrrolidone-vinyl acetage [sic] (65/35) copolymer sold under the name "RESINE PVP/VA S 630 L" by the company GAF | | 10 g |
| Compound of Example 2 | | 0.25 g |
| Poly(hydroxypropyl ether) prepared by condensation, under alkaline catalysis, of 3.5 mol of glycidol with a mixture of alpha-diols having 10 to 14 carbons | | 0.1 g |
| Ethyl alcohol | | 45.2 g |
| Fragrance, dye, preserving agent | qs | |
| Demineralized water | qs | 100 g |

Spontaneous pH of 4.9.

An opalescent solution is obtained.

Example P

Styling Mousse

An aerosol styling mousse having the following composition is prepared:

| | | |
|---|---|---|
| Hydroxyethylcellulose diallyldimethyl-ammonium chloride copolymer "CELQUAT LOR" [lacuna] by the company NATIONAL STARCH | | 1 g |
| Compound of Example 6 | | 0.2 g |
| Ethyl alcohol | | 17.3 g |
| Oxyethylenated octylphenol containing 10 mol of ethylene oxide, sold under the name "SCUROL O" by the company SFOS | | 0.2 g |
| Fragrance, dye, preserving agent | qs | |
| Water | qs | 100 g |

90 g of the composition obtained are introduced into an aerosol container with plunger tube. The valve is attached and the receptacle is closed hermetically, followed by introduction of 10 g of a butane/isobutane/propane propellant mixture (0.32 MPa (3.2 bar)).

Example Q

A reducing composition for the permanent reshaping of the hair is prepared by mixing the following ingredients:

Reducing composition:

| | | |
|---|---|---|
| Compound of Example 2 | | 0.25 g |
| Oxyethylenated octylphenol containing 10 mol of ethylene oxide, sold under the name "SCUROL O" by the company SFOS | | 2 g |
| Hot demineralized water | | 60 g |
| Thioglycolic acid | | 9 g |
| 20% aqueous ammonia | qs | pH 8.2 |
| Demineralized water | qs | 100 g |

This composition is applied to wet hair which has been wound beforehand on rollers. After allowing the composition to act for 15 minutes, the hair is rinsed thoroughly with water and the following composition is then applied:

Oxidizing composition:

| | | |
|---|---|---|
| Hydrogen peroxide | | 1.5 g |
| Oxyethylenated sodium lauryl ether sulfate with 2 mol of ethylene oxide | | 3.75 g |
| Citric acid | | 0.5 g |
| Sodium hydrogen phosphate | | 0.5 g |
| Fragrance | | 0.3 g |
| Demineralized water | qs | 100 g |

The oxidizing composition is allowed to act for about 15 minutes, then the rollers are removed and the head of hair is rinsed thoroughly with water. After drying under a hood, the hair has beautiful curls.

Example R

A permanent reshaping of hair is performed according to the same embodiment of Example Q, using the following reducing composition:

| | | |
|---|---|---|
| Compound of Example 2 | | 0.25 g |
| Oxyethylenated octylphenol containing 10 mol of ethylene oxide, sold under the name "SCUROL O" by the company SFOS | | 2 g |
| Hot demineralized water | | 20 g |
| Glycerol thioglycolate (70% active substance in glycerol) | | 10 g |
| Triethanolmaine [sic] | qs | pH 7 |
| Demineralized water | qs | 100 g |

The oxidizing composition is the same as that of Example Q.

Example S

Tinted Water-In-Oil Care Cream

| | |
|---|---|
| Alkyldimethicone copolyol sold under the name "ABIL EM 90" by the company GOLDSCHMIDT | 5.00 g |
| Stearalkonium hectorite | 2.00 g |
| Octyldodecanol | 8.00 g |
| Decamethylcyclopentasiloxane | 20.00 g |
| Fragrance | qs |
| Preserving agent | qs |
| Glycerine | 3.00 g |
| Pigments | 7.00 g |
| Compound of Example 1 | 0.50 g |

-continued

| | | |
|---|---|---|
| Sodium chloride | | 1.50 g |
| Demineralized water | qs | 100 g |

Example T

Tinted Water-In-Oil Care Cream

| | | |
|---|---|---|
| Magnesium aluminum silicate | | 0.50 g |
| Carboxymethylcellulose | | 0.15 g |
| Propylene glycol | | 5.00 g |
| Preserving agents | qs | |
| Compound of Example 4 | | 1.00 g |
| Lanolin alcohol | | 1.50 g |
| Glyceryl stearate | | 1.00 g |
| Steraric [sic] acid | | 2.50 g |
| Triethanolamine | | 1.50 g |
| Triglycerides of capric/caprylic acid | | 6.00 g |
| Polyisobutene | | 10.00 g |
| Nylon powder | | 3.00 g |
| Pigments | | 10.00 g |
| Demineralized water | qs | 100 g |

Example U

Mascara

| | | |
|---|---|---|
| Triethanolamine stearate | | 15.00 g |
| Paraffin | | 3.00 g |
| Beeswax | | 8.00 g |
| Compound of Example 1 | | 0.50 g |
| Colophane | | 2.00 g |
| Ozokerite | | 10.00 g |
| Preserving agents | qs | |
| Gum arabic | | 0.60 g |
| Keratin hydrolysate | | 1.00 g |
| Pigments | | 6.00 g |
| Demineralized water | qs | 100 g |

Example V

Treatment Base for the Nails

| | | |
|---|---|---|
| Nitrocellulose | | 12.00 g |
| Toluenesulfonamide-formaldehyde resin | | 9.00 g |
| Camphor | | 1.00 g |
| Dibutyl phthalate | | 6.05 g |
| Butyl acetate | | 24.00 g |
| Isopropyl acetate | | 6.00 g |
| Stearalkonium hectorite | | 1.00 g |
| Compound of Example 4 | | 0.01 g |
| Citric acid | | 0.02 g |
| Toluene | qs | 100 g |

Example W

Lipstick

| | |
|---|---|
| Butylhydroxytoluene | 0.20 g |
| Liquid lanolin | 17.50 g |
| Microcrystalline [sic] wax | 15.00 g |
| Triglycerides of capric/caprylic acids | 11.00 g |
| Oxtyl [sic] glyceryl behenate | 11.00 g |
| Pigments | 3.00 g |
| Titanium mica | 6.00 g |

| | | |
|---|---|---|
| Fragrance | | 0.50 g |
| Castor oil | qs | 100 g |

Example X

Lipstick

| | | |
|---|---|---|
| Fragrance | | 0.50 g |
| Triglycerides of capric/caprylic acids | | 9.10 g |
| Castor oil | | 9.10 g |
| Butylhydroxytoluene | | 0.16 g |
| Liquid lanolin | | 12.70 g |
| Isopropyl lanolin | | 4.50 g |
| Compound of Example 1 | | 0.50 g |
| Microcrystalline wax | | 11.00 g |
| Vinyl acetate/allyl stearate (65/35) copolymer | | 4.50 g |
| Octyl glyceryl behenate | | 9.10 g |
| Pigments | | 9.00 g |
| Sesame oil | qs | 100 g |

Example Y

Conditioner

| | | |
|---|---|---|
| Distearyldimethylammonium chloride | | 2.00 g |
| Compound of Example 5 | | 0.5 g |
| N-(Hydroxymethyl)-N-(1,3-dihydroxymethyl-2,5-dioxo-4-imidazolidinyl)-N'-(hydroxymethyl)urea | | 0.1 g |
| Water | qs | 100 g |

Spontaneous pH: 4

We claim:

1. Cosmetic composition for the cosmetic treatment of keratinous substances in the form of an emulsion, a vesicle dispersion, a powder, an aqueous dispersion, an aqueous solution, an aerosol foam or spray, consisting essentially of, in a cosmetically acceptable medium, at least one lipophilic derivative of amino deoxyalditol corresponding to the formula:

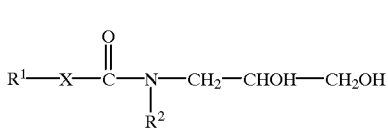

(I)

in which:

$R^1$ is a saturated linear $C_{14}$–$C_{40}$ aliphatic radical;

$R^2$ is a hydrogen atom or a linear $C_1$–$C_6$ alkyl radical;

X is an oxygen atom; and n is an integer from 1 to 5, and a cosmetic adjuvant selected from the group consisting of oils, waxes, emulsifying agents, solvents, thickening agents, moisturizing agents, emollients, suscreen agents, germicides, dyes, preserving agents, fragrances, propellants and sequestering agents.

2. Composition according to claim 1, wherein $R^1$ is a saturated linear $C_{14}$–$C_{32}$ aliphatic radical.

3. Composition according to claim 1, wherein $R^1$ is a linear $C_{21}$–$C_{29}$ aliphatic radical.

4. Composition according to claim 1, wherein $R^2$ is a methyl radical.

5. Composition according to claim 1, wherein the derivative or derivatives of formula (I) are present at a concentration between 0.01 and 15% by weight relative to the total weight of the composition.

6. Composition according to claim 1, which is provided in the form of a lotion, a milk or a cream a shampoo, or a conditioner.

7. Composition according to claim 1, wherein the derivative or derivatives of formula (I) are present at a concentration between 0.1 and 10% by weight relative to the total weight of the composition.

8. Composition according to claim 1, wherein said cosmetically acceptable medium is selected from the group consisting of water and a mixture of water and a cosmetically acceptable solvent.

9. Hair treating cosmetic composition in the fort of an emulsion, a vesicle dispersion, a powder, an aqueous dispersion, an aqueous solution, an aerosol foam or spray, consisting essentially of, in a cosmetically acceptable medium, at lest one hair conditioning lipophilic derivative of amino deoxyalditol corresponding to the formula:

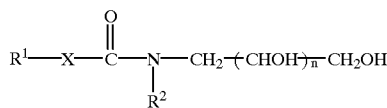

(I)

in which:

$R^1$ is a saturated linear $C_{14}$–$C_{40}$ aliphatic radical;

$R^2$ is a hydrogen atom or a linear $C_1$–$C_6$ alkyl radical;

X is an oxygen atom; and n is an integer from 1 to 5, and a cosmetic adjuvant selected from the group consisting of oils, waxes, emulsifying agents, solvents, thickening agents, moisturizing agents, emollients, sunscreen agents, germicides, dyes, preserving agents, fragrances, propellants and sequestering agents.

10. Composition according to claim 9, wherein $R^1$ is a saturated linear $C_{14}$–$C_{32}$ aliphatic radical.

11. Composition according to claim 9, wherein $R^1$ is a linear $C_{21}$–$C_{29}$ aliphatic.

12. Composition according to claim 9, wherein $R^2$ is a methyl radical.

13. Composition according to claim 9 wherein the derivative or derivatives of formula (I) are present at a concentration between 0.01 and 15% by weight relative to the total weight of the composition.

14. Composition according to claim 9 which is provided in the form of a lotion, a milk or a cream, a shampoo or a conditioner.

15. Composition according to claim 9, wherein the derivative or derivatives of formula (I) are present at a concentration between 0.1 and 10% by weight relative to the total weight of the composition.

16. Composition according to claim 9, wherein said cosmetically acceptable medium is selected from the group consisting of water and a mixture of water and a cosmetically acceptable solvent.

17. Skin treating cosmetic composition in the form of an emulsion, a vesicle dispersion, a powder, an aqueous dispersion, an aqueous solution, an aerosol foam or spray, consisting essentially of, in a cosmetically acceptable medium, at least one lipophilic derivatives of amino deoxyalditol corresponding to the formula:

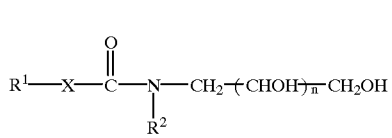

(I)

in which:

$R^1$ is a saturated linear $C_{14}$–$C_{40}$ aliphatic radical;

$R^2$ is a hydrogen atom or a linear $C_1$–$C_6$ alkyl radical;

X is an oxygen atom; and n is an integer from 1 to 5, and a cosmetic adjuvant selected from the group consisting of oils, waxes, emulsifying agents, solvents, thickening agents, moisturizing agents, emollients, sunscreen agents, germicides, dyes, preserving agents, fragrances, propellants and sequestering agents.

18. Composition according to claim 17, wherein $R^1$ is a saturated linear $C_{14}$–$C_{32}$ aliphatic radical.

19. Composition according to claim 17, wherein $R^1$ is a linear $C_{21}$–$C_{29}$ aliphatic.

20. Composition according to claim 17, wherein $R^2$ is a methyl radical.

21. Composition according to claim 17 wherein the derivative or derivatives of formula (I) are present at a concentration between 0.01 and 15% by weight relative to the total weight of the composition.

22. Composition according to claim 17 which is provided in the form of a lotion, a milk or a cream, a milk for removing make-up, a foundation base, an anti-sun lotion, an anti-sun milk or cream, an artificial tanning lotion, an artificial tanning milk or cream, a shaving cream or foam, an after-shave lotion, a conditioner or a mascara.

23. Composition according to claim 17, wherein the derivative or derivatives of formula (I) are present at a concentration between 0.1 and 10% by weight relative to the total weight of the composition.

24. Composition according to claim 17, wherein said cosmetically acceptable medium is selected from the group consisting of water and a mixture of water and a cosmetically acceptable solvent.

* * * * *